US012588835B2

(12) United States Patent
Oliveira Santos et al.

(10) Patent No.: US 12,588,835 B2
(45) Date of Patent: Mar. 31, 2026

(54) METHOD AND SYSTEM FOR TRACKING MOVEMENT OF A PERSON WITH WEARABLE SENSORS

(71) Applicant: SWORD HEALTH S.A., Oporto (PT)

(72) Inventors: Pedro Henrique Oliveira Santos, Oporto (PT); Ivo Emanuel Marques Gabriel, Oporto (PT); Luís Ungaro Pinto Coelho, Oporto (PT); Marta Maria Ramalho Ferreira, Oporto (PT); Ana Clara Ferreira Matos, Oporto (PT); Virgílio António Ferro Bento, Oporto (PT)

(73) Assignee: SWORD HEALTH, S.A., Oporto (PT)

( * ) Notice: Subject to any disclaimer, the term of this patent is extended or adjusted under 35 U.S.C. 154(b) by 1164 days.

(21) Appl. No.: 17/598,687

(22) PCT Filed: Mar. 23, 2020

(86) PCT No.: PCT/EP2020/058014
§ 371 (c)(1),
(2) Date: Sep. 27, 2021

(87) PCT Pub. No.: WO2020/200891
PCT Pub. Date: Oct. 8, 2020

(65) Prior Publication Data
US 2022/0183592 A1    Jun. 16, 2022

(30) Foreign Application Priority Data
Mar. 29, 2019    (EP) ..................................... 19398003

(51) Int. Cl.
*A61B 5/11*          (2006.01)
(52) U.S. Cl.
CPC ..... *A61B 5/1126* (2013.01); *A61B 2562/0219* (2013.01); *A61B 2562/04* (2013.01)

(58) Field of Classification Search
CPC .......... A61B 5/1126; A61B 2562/0219; A61B 2562/04; A61B 5/1121; A61B 5/1123;
(Continued)

(56) References Cited

U.S. PATENT DOCUMENTS

2008/0262772 A1* 10/2008 Luinge ................. A61B 5/4528
                                                                            702/94
2009/0322763 A1* 12/2009 Bang ...................... G06V 40/23
                                                                            73/865.4
(Continued)

FOREIGN PATENT DOCUMENTS

EP          3714786          9/2020
EP          3946048          2/2022
(Continued)

OTHER PUBLICATIONS

Duk-Jin Kim et al, "Motion fault detection and isolation in Body Sensor Networks", Pervasive and Mobile Computing, Mar. 21, 2011, vol. 7, No. 6, pp. 727-745, XP028121069.
(Continued)

*Primary Examiner* — Tse W Chen
*Assistant Examiner* — Evelyn Grace Park
(74) *Attorney, Agent, or Firm* — SCHWEGMAN LUNDBERG & WOESSNER, P.A.

(57) ABSTRACT

Methods and systems for tracking movement of a person, includes: arranging sensors of a motion tracking system on a person; tracking movement with the sensors at least while the person performs a movement; digitally estimating, with a computing device, a position of the first joint or the sensor on the second body member, wherein the position of the first joint is estimated using measurements of the first sensor and its position is estimated using measurements of the first sensor and the sensor arranged on the second body member. The position is estimated while the movement is tracked.
(Continued)

The method further includes digitally computing, an acceleration of the estimated position while movement is tracked; digitally computing a first comparison between the computed acceleration of the estimated position and acceleration measurements of the sensor arranged on the second body member; and digitally determining the movement performed based on the first comparison.

18 Claims, 6 Drawing Sheets

(58) Field of Classification Search
    CPC ..... A61B 5/1124; A61B 5/6813; A61B 5/684;
                     A61B 5/7221; A61B 5/1116; A61B
                                                5/11–113
    See application file for complete search history.

(56)                    References Cited

U.S. PATENT DOCUMENTS

| | | | |
|---|---|---|---|
| 2016/0058326 A1 | 3/2016 | Winfree et al. | |
| 2017/0027498 A1 | 2/2017 | Larson et al. | |
| 2017/0086711 A1 | 3/2017 | Liao et al. | |
| 2018/0070864 A1* | 3/2018 | Schuster | G16H 40/63 |
| 2018/0317779 A1 | 11/2018 | Gregg et al. | |
| 2020/0146594 A1* | 5/2020 | Gong | A61B 5/7275 |

FOREIGN PATENT DOCUMENTS

| | | |
|---|---|---|
| EP | 4122393 | 1/2023 |
| EP | 4241660 | 9/2023 |
| WO | WO-2020200891 A1 | 10/2020 |

OTHER PUBLICATIONS

Iman Prayudi et al, "Design and implementation of IMU-based human arm motion capture system", Mechatronics and Automation (ICMA), 2012 International Conference on, IEEE, Aug. 5, 2012, pp. 670-675, XP032224400.

International Search Report May 25, 2020 re: Application No. PCT/EP2020/058014, pp. 1-7, Lin et al. "Human pose recovery . . . ", Boonstra et al. "The accuracy of measuring . . . ", US 2016/0058326 A1, US 2017/0086711 A1, US 2017/0027498 A1, Kim et al. "Motion fault detection . . . ", Prayudi et al., "Design and implementation . . . " and US 2018/0317779 A1.

Jonathan F S Lin et al, "Human pose recovery using wireless inertial measurement units", Physiological Measurement, Institute of Physics Publishing (IOP), Nov. 23, 2012, vol. 33, No. 12, pp. 2099-2115, XP020234074.

Miranda C. Boonstra et al, "The accuracy of measuring the kinematics of rising from a chair with accelerometers and gyroscopes", Journal of Biomechanics, Dec. 1, 2006, vol. 39, No. 2, pp. 354-358, XP055617281.

Written Opinion May 25, 2020 re: Application No. PCT/EP2020/058014, pp. 1-17, Lin et al. "Human pose recovery . . . ", Boonstra et al. "The accuracy of measuring . . . ", US 2016/0058326 A1, US 2017/0086711 A1, US 2017/0027498 A1, Kim et al. "Motion fault detection . . . ", Prayudi et al., "Design and implementation . . . " and US 2018/0317779 A1.

EP Application No. 19398003.4 Extended European Search Report dated Dec. 2, 2019.

EP Application No. 22194750.0 Extended European Search Report dated Nov. 28, 2022.

European Application Serial No. 23184728.6, Response filed Oct. 25, 2024 to Communication Pursuant to Article 94(3) EPC mailed Jun. 25, 2024, 22 pgs.

"European Application Serial No. 23184728.6, Extended European Search Report mailed Oct. 16, 2023", 8 pgs.

"European Application Serial No. 22194750.0, Communication Pursuant to Article 94(3) EPC mailed Nov. 13, 2023", 4 pgs.

"International Application Serial No. PCT EP2020 058014, International Preliminary Report on Patentability mailed Oct. 14, 2021", 19 pgs.

"European Application Serial No. 19398003.4, Partial Supplementary European search report mailed Sep. 13, 2019", 8 pgs.

"European Application Serial No. 22194750.0, Response filed Jul. 18, 2023 to Extended European Search Report mailed Dec. 5, 2022", 14 pgs.

"European Application Serial No. 20713622.7, Response to Communication pursuant to Rules 161(1) and 162 EPC filed May 11, 2022", 37 pgs.

"European Application Serial No. 20713622.7, Intention to Grant mailed Sep. 30, 2022", 5 pgs.

"European Application Serial No. 20713622.7, Response filed Jan. 17, 2023 to Intention to Grant mailed Sep. 30, 2022", 3 pgs.

"European Application Serial No. 20713622.7, Intention to Grant mailed Feb. 8, 2023", 5 pgs.

"European Application Serial No. 19398003.4, Noting of loss of rights pursuant to Rule 112(1) EPC mailed Apr. 23, 2021", 2 pgs.

"European Application Serial No. 22194750.0, Response filed Feb. 22, 2024 to Communication Pursuant to Article 94(3) EPC mailed Nov. 13, 2023", 13 pgs.

"European Application Serial No. 23184728.6, Communication Pursuant to Article 94(3) EPC mailed Jun. 25, 2024", 7 pgs.

"European Application Serial No. 23184728.6, Response filed Feb. 19, 2024 to Communication Pursuant to R.70a(1) EPC mailed Nov. 20, 2023", 14 pgs.

European Application Serial No. 23184728.6, Summons to Attend Oral Proceedings mailed Feb. 5, 2025, 5 pgs.

* cited by examiner

50

22

21

56

61

63

64

23

METHOD AND SYSTEM FOR TRACKING MOVEMENT OF A PERSON WITH WEARABLE SENSORS

TECHNICAL FIELD

The present invention relates to the field of motion tracking of a person. More specifically, the present invention relates to the determination of tracked motion of the person when wearable motion tracking sensors are used.

STATE OF THE ART

Motion tracking or motion capture of a target is a technical process used in many applications, such as, control of machines, automatization of processes, or gait analysis to name a few. The motion of a person or an object is usually tracked by means of sensors that are attached to the person or object, or by means of image/video digital analysis.

Personal physical exercise and physical rehabilitation are applications that rely on motion tracking and which are becoming more and more popular. A person may train or do physical therapy at some premises (e.g. at home) without the direct supervision of a trainer or a therapist, for example, yet being able to review her/his own physical exercises or provide information about the same to the trainer or the therapist, thanks to motion tracking.

When sensors are the source of motion information, as each sensor operates independently from the others, the measurements of the sensors have to be processed in such a way that the movement performed by the person is determined based on all the measurements. In contrast to the motion tracked based on images or video in which, oftentimes, all the body members tracked or even the entire person tracked are present in each image or frame, in the motion tracked with a plurality of wearable sensors each sensor only provides data regarding the movement of a part of the person. Therefore, the measurements are processed so that the combination of all the measurements provides information about the movement performed by the person.

In some cases, processing techniques of the state of the art do not suffice to determine the movement performed by the person. For example, in a movement involving a kinematic chain of the person it can be complex to know from the sensor measurements whether one member or another of the kinematic chain has moved since similar measurements are potentially provided by the sensors when two different movements involving that chain are performed; for instance, it can be complex to determine whether an extremity of the kinematic chain moves or is static. Thus, more advanced processing techniques are necessary.

Further, albeit such processing is necessary for determining the movement performed by the person, it is also important to know where each sensor is placed on the target as that affects the determination of the movement. In this sense, the computing device receiving all the sensor data and generating an output corresponding to the motion tracked must be provided with data indicative of the placement of the sensors on the target, otherwise the motion of the different parts of the target will be out of position, something that may ultimately render the motion tracked useless. When individual sensors have to be placed on the target or person, the person may inadvertently swap the placement of several sensors on her/his body or register in the computing device an incorrect sensor correspondence between the sensors placement and the data introduced in the computing device.

These problems affect the effectiveness of motion tracking for both personal physical exercises and physical rehabilitation because incorrect movement determination results in wrong exercise assessments, which entails the risk of injuries for the person exercising.

It would be advantageous to have a way to process measurements of motion tracking sensors so that the movement of a tracked person is properly determined by a computing device. It would be advantageous too to have a way to process measurements of motion tracking sensors so that it can be determined whether the person has the motion tracking sensors arranged thereon in a way that does not correspond to a registered sensor arrangement.

DESCRIPTION OF THE INVENTION

A first aspect of the invention relates to a method for tracking movement of a person, the method comprising the steps of:

arranging a plurality of sensors of a motion tracking system on a body of the person, the plurality of sensors at least comprising first, second and third sensors each at least comprising an accelerometer and a gyroscope, the first sensor being arranged on a first body member of the person, a first one of the second and third sensors being arranged on a second body member of the person, and a second one of the second and third sensors being arranged on a third body member of the person, the first and second body members being connected by a first joint;

tracking movement of the person with the plurality of sensors;

digitally estimating, with a computing device, a position of either the first joint or the sensor on the second body member, the position of the first joint being estimated using measurements of the first sensor and the position of the sensor being estimated using measurements of both the first sensor and the sensor arranged on the second body member, and the position being estimated while movement of the person is tracked;

digitally computing, with the computing device, an acceleration of the estimated position while movement of the person is tracked;

digitally computing, with the computing device, a first comparison between the computed acceleration of the estimated position and acceleration measurements of the sensor arranged on the second body member; and digitally determining, with the computing device, the movement performed by the person based on the first comparison.

The processing carried out by the computing device allows to determine which movement the person has performed that involves motion of one, some or all of the first, second and third body members.

The measurements of each sensor are at least the orientation and acceleration of the sensor. These measurements, however, need to be assessed together with the measurements of the remaining sensors since the motion of one body member with a sensor thereon usually plays a role on the motion of the other body members with sensors thereon. For example, when moving the upper arm, the lower arm is displaced together with the upper arm, but when the lower arm moves the upper arm is not necessarily displaced as well.

There are different types of movements that result in a similar relative arrangement of some body members involved at one moment during the movement, for example at the end of two or more different movements there may be two, three or more body members that have same or similar angular positions between them, and it is complex to be able to digitally distinguish such types of movements with the measurements provided by the sensors; visually, however, one could easily tell which movement has been actually performed.

In order to distinguish these types of movements which involve motion of one, some or all of the first, second and third body members, the position of either the first joint or the sensor on the second body member is estimated as the combination of the first and second body members together with the first joint form a kinematic chain. Preferably, the position of the end of the first body member not connected to the second body member is known; in the context of the present disclosure, knowing the position of an end of a body member refers to modelling or estimating said position so that the computing device may use said modelled or estimated position as origin of the referential for the positions and accelerations. Also, the position of said end is preferably still or substantially still while the person performs the movement.

If the computing device estimates the position of the first joint, the estimation is based on the measurements provided by the first sensor, and preferably also based on a first predetermined length value that corresponds to the first body member, particularly to the length thereof. By way of example, with the orientation of the first sensor on the first body member and the first predetermined length, the position of the first joint relative to a reference point (having a known position) of the first body member is estimated. For instance, if the first body member is the upper leg and the second body member is the lower leg, the orientation of the first sensor is indicative of the orientation of the upper leg, and from which it is estimated where the knee is (i.e. first joint) relative to the hip (i.e. reference point) by means of a possible length for the upper leg (i.e. first predetermined length). By way of another example in which the reference point does not have a known position, the procedure is carried out similarly since the position of the knee is estimated relative to a reference point defined also by the orientation of the first sensor; when the orientation of the first sensor is considered together with a certain length value so as to digitally provide a body member, one end of this digital version of the body member is a reference point and the other end of this digital version of the body member is a point of the first joint, thus by way of the orientation and length of the digital version of the body member the position of the point of the first joint is known relative to the reference point.

If the computing device estimates the position of the sensor on the second body member (e.g. the second sensor), the estimation is based on the measurements provided by both the first sensor and said sensor on the second body member, and preferably also based on first and second predetermined length values that correspond to the first and second body members, particularly to the lengths thereof. By way of example, with the orientation of the first sensor on the first body member and the first predetermined length, the position of the first joint relative to a reference point of the first body member is estimated. Then, with the orientation of the sensor on the second body member and the second predetermined length, the position of the sensor relative to the reference point is estimated. For instance, the orientation of the sensor on the second body member is indicative of the orientation of the lower leg, and from which it is estimated where the sensor is relative to the knee (i.e.

first joint) by means of a possible length for the lower leg (i.e. second predetermined length), whose value is adjusted by a factor in the form of a decimal number greater than 0 and smaller than 1 depending on the expected position of the sensor on the lower leg (because it is placed between the knee and the ankle); the complete processing thus provides an estimated position for said sensor with respect to the hip (i.e. reference point), since that is the reference point from which the positions are estimated. In some cases, the second predetermined length is selected such that it corresponds to the length from the first joint to the expected placement of the sensor on the second body member, that is to say, it corresponds to the estimated length of the second body member multiplied by the factor.

Then, the computing device estimates the acceleration of said estimated position, which is done by computing the second derivative of the estimated position. Accordingly, the position estimation is performed while the movement is tracked (as subsequent measurements are received from the sensors, the position estimation is recomputed), so the position is updated during the process and, therefore, the estimated acceleration can be computed. Preferably, the position and the acceleration are both estimated by the computing device considering that the end of the first body member opposite to the end connected to the first joint is still or substantially still for a more accurate estimation, thus the computing device preferably performs said estimations modelling said end not connected to the first joint as being still or substantially still.

The comparison between the computed acceleration of the estimated position and acceleration measurements of the sensor (provided by the accelerometer thereof) arranged on the second body member is used for determining how at least the first and second body members have moved with respect to the body of the person. This determination thus disambiguates movements that result in body members having same or similar relative angular positions at one point during the movement, and therefore it is possible to determine which is the movement performed by the person based on the measurements provided by the sensors placed thereon. In order to do so, a predetermined threshold is set in the computing device, and the result of the comparison is compared to the predetermined threshold to carry out the movement determination.

The first and second predetermined lengths, and the factor used, can be selected based on statistics, average lengths, etc., or input of the same may be requested prior to tracking motion (e.g. the person introduces the values with user input means such as a touchscreen, keyboard, etc.), or digitally estimated with the computing device using image or video footage (provided by optical sensors) of the person whose motion is to be tracked. Even though it is desirable to have predetermined values being as close as possible to the actual lengths so that the movement as determined by the computing device is more accurate, with other values differing from the actual values the computing device is also capable of determining the movement.

In some cases, the computing device provides two sets of data: a first one with the motion tracking as determined from the sensor measurements as known in the art, and a second one with data relative to the movement actually performed. That is to say, the computing device provides motion tracking without adjusting the movement of the body members, and also provides information about the movement performed in terms of which body members have moved and how, the latter being important for disambiguating similar movements and/or detecting which body members of a kinematic chain have moved or remained static; without this information, some movements cannot be determined just with the first set of data if the same is not processed according to the present method. In this sense, if these data are sent to a therapist, the therapist has all the information necessary to know which movements have been performed by the person, otherwise the provision of the first set of data without any further processing is not sufficient for inferring which movements have been actually performed by the person.

In some other cases, the computing device only provides the second set of data relative to the movement actually performed. For example, when motion is being tracked by means of another motion tracking procedure or a second computing device, the measurements may be passed on to the computing device so as to disambiguate similar movements and/or detect which body members of a kinematic chain have moved or remained static, and provide that information to any device (e.g. second computing device) or person that may use it together with the motion tracking data provided by the another motion tracking procedure or the second computing device. By way of example, the second set of data can be used in other procedures that combine it with other motion tracking data so as to assess the performance of the person and generate more digested information (e.g. correctness or accuracy of the movements of the therapy or training routine and performed by the person, reasons why movements are not being correctly performed, etc.) for a therapist or a personal trainer that supervises exercises of the person.

In some embodiments, the step of digitally determining the movement comprises determining that a first predetermined movement has been performed by the person if the first comparison is above a predetermined threshold. In some of these embodiments, the step of digitally determining the movement further comprises determining that either the first predetermined movement has not been performed by the person or a second predetermined movement has been performed by the person if the first comparison is below the predetermined threshold.

If the result of the comparison is above the predetermined threshold set, it is determined that the movement performed is the one for which the predetermined threshold was set, whereas if the result of the comparison is below the predetermined threshold set, then it is determined that the movement performed is not the one for which the predetermined threshold was set. In this latter case, in some examples the computing device not only determines that the movement performed is not the one for which the predetermined threshold was set, but also determines that the movement performed is another particular movement, e.g. a movement resulting in a similar angular relationship between the sensed body members but resulting in a comparison not exceeding the predetermined threshold set.

It is readily apparent that the predetermined threshold may be set in the opposite way. That is to say, the predetermined threshold is set so that if the comparison is below the predetermined threshold it is determined that the first movement has been performed, whereas if the comparison is above the predetermined threshold, it may be determined that the first movement has not been performed or the second predetermined movement has been performed.

In some embodiments, the method further comprises: digitally computing, with the computing device, a second comparison between the computed acceleration of the estimated position and acceleration measurements of the sensor arranged on the third body member; and digitally determining, with the computing device, whether the second and third sensors have been arranged on the second and third body members, respectively, based on both the first and second comparisons.

When the computing device has data indicative of the movement to be performed by the person, for example when the motion tracking procedure is for performing particular physical exercises and/or physical rehabilitation, the data can be processed by the computing device to know which body members have to move and how; this, in turn, makes possible to determine how the sensors have been arranged on the person. For instance, if the movement involves moving the upper arm upwards, the lower arm is also to move upwards.

By way of the first and second comparisons, the computing device has data relative to how each of the second and third sensors compares to the computed acceleration of the estimated position and can thus determine if the second sensor is arranged on the second body member and the third sensor is arranged on the third body member, as it would expect in accordance with a registered correspondence between sensors and body members (also referred to in the present disclosure as sensor arrangement). The computing device expects the estimated acceleration to be more or less similar to the acceleration measurements of the second sensor (preferably the acceleration measurements fall within a range of 0,8 times Acc to 1,2 times Acc, where Acc is the estimated acceleration, and more preferably within a range of 0,9 times Acc to 1,1 times Acc), or at least more similar to the acceleration measurements of the second sensor than to the acceleration measurements of the third sensor (i.e. a difference between the estimated acceleration and the acceleration measurements of the second sensor is less than a difference between the estimated acceleration and the acceleration measurements of the third sensor). If this is the case, the computing device identifies the second sensor as the sensor arranged on the second body member, and the third sensor as the sensor arranged on the third body member, hence the registered correspondence matches the actual sensor placement. The correspondence determined by the computing device is also made even when, for example in some embodiments, one of the sensors is not arranged on the second body member, or the other one of the sensors is not arranged on the third body member (for instance, one of these sensors has been left on a charging station or on a table as users sometimes inadvertently do), since the computing device will process the measurements of both sensors and determine which one has provided measurements that are more similar to the expected movement to be performed by the concerned body members than the other sensor.

In some embodiments, if it is digitally determined that the second and third sensors have been arranged on the third and second body members, respectively, the computing device digitally substitutes measurements of the second sensor for measurements of the third sensor and/or vice versa while movement of the person is tracked.

Neither the person needs to interchange the second and third sensors even though they have been placed on the person swapped nor the motion tracking procedure needs to be stopped. The computing device has determined that the sensors have been swapped, and so by substituting the measurements of the second and third sensors (i.e. the measurements of the second sensor are regarded as the measurements of the third sensor, and/or the measurements of the third sensor are regarded as the measurements of the second sensor) the motion tracking procedure is carried out as if the sensors had not been swapped. If the person were to change the placement of the sensors because they were swapped, the person could inadvertently place the sensors thereon swapped once again, thereby affecting the correctness of the motion tracking.

In some embodiments, the step of digitally determining whether the second and third sensors have been arranged on the second and third body members, respectively, is carried out prior to the step of digitally determining the movement performed by the person based on the first digital comparison.

When it is not registered which of the second and third sensors is arranged on the second and third body members, it is convenient to first determine if said sensors are arranged on the respective body members. Then, the computing device determines the movement performed by the person based on the determined sensor arrangement so that it may properly disambiguate similar movements and/or detect which body members of a kinematic chain have moved or remained static.

In some embodiments, each comparison is digitally computed so that a result thereof is indicative of a level of similarity or dissimilarity between the computed acceleration of the estimated position and the acceleration measurements of the corresponding sensor of the plurality of sensors.

The comparison(s) may be established in terms of similarity or dissimilarity between the compared values as known in the art. The predetermined threshold is set in accordance with the type of result of the comparison(s), that is to say, set depending on whether it is indicative of the level of similarity or the level of dissimilarity. Also, as aforementioned, the predetermined threshold may be set so that the value thereof should be exceeded or not exceeded to determine that the first movement has been performed by the person when the result of the comparison is indicative of the level of similarity or dissimilarity.

By way of example, the comparison(s) may be: the dot product between the two signals in a given time window, the dot product in the frequency domain, the cross correlation between the two signals (evaluated at t=0), the mean squared difference, etc.

In some embodiments, the computing device digitally determines that the second and third sensors have been arranged on the second and third body members, respectively, if the result of the first comparison is: greater than the result of the second comparison if both results are indicative of a level of similarity; or lower than the result of the second comparison if both results are indicative of the level of dissimilarity. In some of these embodiments, if the result of the first comparison does not fulfill any one of these criteria, the computing device digitally determines that the second and third sensors have been arranged on the third and second body members, respectively.

In some embodiments: the position of the first joint is digitally estimated by processing measurements of the first sensor and a first predetermined length; and the position of the sensor arranged on the second body member is digitally estimated by processing measurements of both the first sensor and the sensor arranged on the second body member and both the first and a second predetermined lengths. In some of these embodiments, the position of the sensor arranged on the second body member is digitally estimated by further processing a factor in the form of a decimal number greater than 0 and smaller than 1.

In some embodiments, movement of the person is tracked with the plurality of sensors at least while the person performs a movement. In some of these embodiments, the movement involves the first body member and at least one of the second and third body members. In some of these embodiments, the movement involves each of the first, second and third body members.

The person can be requested to perform a movement through presenting means, e.g. a screen visually showing instructions or a representation of the movement, audio output means providing audio instructions or guidance of the movement, etc.

In some embodiments, the first body member undergoes a rotation greater than rotation/s of the second and/or third body members during the movement.

In some embodiments, the first and second body members are, respectively: upper leg and lower leg; lower leg and upper leg; upper arm and lower arm; chest and upper arm; lower back and upper back; upper chest and head; upper chest and upper arm; lower chest and upper chest; lower arm and hand; hand and fingers; lower leg and foot; foot and toes; lower arm and upper arm; upper leg and chest; upper arm and chest; or head and chest.

In some embodiments, the first body member is a body member different from an extremity.

In some embodiments, the first and second body members form a kinematic chain with the third body member. In some of these embodiments, the third body member is connected to the first body member by a second joint. In some other embodiments, the third body member is connected to the second body member by a second joint.

In some embodiments, all the body members having a sensor arranged thereon form a kinematic chain.

A second aspect of the invention relates to a system for tracking movement of a person, comprising:

a plurality of sensors at least comprising first, second and third sensors each at least comprising an accelerometer and a gyroscope, the first sensor being arrangeable on a first body member of the person, a first one of the second and third sensors being arrangeable on a second body member of the person, and a second one of the second and third sensors being arrangeable on a third body member of the person; and a computing device comprising at least one processor, at least one memory and means for transmitting and receiving data, the computing device being programmed to:

estimate either a position of a first joint connecting the first and second body members or a position of the sensor on the second body member when the person has the plurality of sensors arranged thereon tracking the movement of the person, the position of the first joint being estimated using measurements of the first sensor and the position of the sensor being estimated using measurements of both the first sensor and the sensor arranged on the second body member;

compute an acceleration of the estimated position while movement of the person is tracked;

compute a first comparison between the computed acceleration of the estimated position and acceleration measurements of the sensor arranged on the second body member; and determine the movement performed by the person based on the first comparison.

The system comprises the plurality of sensors and the computing device for the motion tracking of the person. The sensors of the plurality of sensors are attachable to the body of the person so that, while worn by the person, each one of them provides measurements relative to the acceleration and orientation of the body member the sensor is attached to.

The computing device is configured to determine the movement that is performed by the person owing to the sensor measurements and digital processing thereof. The computing device therefore makes possible to disambiguate similar movements and/or detect which body members of a kinematic chain have moved or remained static.

In some embodiments, the computing device determines that a first predetermined movement has been performed by the person if the first comparison is above a predetermined threshold. In some of these embodiments, the computing device further determines that either the first predetermined movement has not been performed by the person or a second predetermined movement has been performed by the person if the first comparison is below the predetermined threshold.

In some embodiments, the computing device is further programmed to: compute a second comparison between the computed acceleration of the estimated position and acceleration measurements of the sensor arranged on the third body member; and determine whether the second and third sensors have been arranged on the second and third body members, respectively, based on both the first and second comparisons.

In some embodiments, the computing device is further programmed to substitute measurements of the second sensor for measurements of the third sensor and/or vice versa while movement of the person is tracked and when the computing device determines that the second and third sensors have been arranged on the third and second body members, respectively.

In some embodiments, the computing device determines whether the second and third sensors have been arranged on the second and third body members, respectively, prior to determining the movement performed by the person based on the first digital comparison.

In some embodiments, the computing device computes each comparison so that a result thereof is indicative of a level of similarity or dissimilarity between the computed acceleration of the estimated position and the acceleration measurements of the corresponding sensor of the plurality of sensors.

In some embodiments, the computing device determines that the second and third sensors have been arranged on the second and third body members, respectively, if the result of the first comparison is: greater than the result of the second comparison if both results are indicative of a level of similarity; or lower than the result of the second comparison if both results are indicative of the level of dissimilarity. In some of these embodiments, if the result of the first comparison does not fulfill any one of these criteria, the computing device determines that the second and third sensors have been arranged on the third and second body members, respectively.

In some embodiments, the computing device estimates: the position of the first joint by processing measurements of the first sensor and a first predetermined length; and the position of the sensor arranged on the second body member by processing measurements of both the first sensor and the sensor arranged on the second body member and both the first and a second predetermined lengths. In some of these embodiments, the computing device estimates the position of the sensor arranged on the second body member by further processing a factor in the form of a decimal number greater than 0 and smaller than 1.

In some embodiments, the system further comprises means for presenting a movement to be performed by the person. In some of these embodiments, the means comprise a screen and/or audio output means.

In some embodiments, the system further comprises user input means, and the computing device is further programmed to receive input for one or more of: the first predetermined length, the second predetermined length, and the factor. In some of these embodiments, the user input means comprise a touchscreen and/or a keyboard.

Similar advantages as those described for the first aspect of the invention are also applicable to this aspect of the invention.

A third aspect of the invention relates to a method for tracking movement of a person, the method comprising the steps of:

arranging a plurality of sensors of a motion tracking system on a body of the person, the plurality of sensors at least comprising first, second and third sensors each at least comprising an accelerometer and a gyroscope, a first one of the first, second and third sensors being arranged on a first body member of the person, a second one of the first, second and third sensors being arranged on a second body member of the person, and a third one of the first, second and third sensors being arranged on a third body member of the person, the first and second body members being connected by a first joint, and the third body member being preferably connected to one of the first and second body members by a second joint;

tracking movement of the person with the plurality of sensors at least while the person performs a movement, the movement performed by the person involving the first body member and at least one of the second and third body members, and the first body member undergoing a rotation greater than rotation/s of the second and/or third body members during the movement;

for each sensor of the plurality of sensors, digitally computing, with a computing device, the rotation undergone by the sensor while movement of the person is tracked;

digitally determining, with the computing device, that the sensor with the greatest computed rotation is arranged on the first body member;

digitally estimating, with the computing device while movement of the person is tracked:
a position of the first joint, the position being estimated using measurements of the determined sensor; or
a position of each of the two other sensors thereby providing first and second estimated positions, the first position being estimated using measurements of both the determined sensor and the first one of the two other sensors, and the second position being estimated using measurements of both the determined sensor and the second one of the two other sensors;

digitally computing, with the computing device, an acceleration of each estimated position while movement of the person is tracked;

digitally computing, with the computing device:
if the estimated position is the position of the first joint, a first comparison between the computed acceleration of the estimated position and acceleration measurements of the first one of the two other sensors, and a second comparison between the computed acceleration of the estimated position and acceleration measurements of the second one of the two other sensors; or
if the estimated position is the first and second estimated positions, a first comparison between the computed acceleration of the first estimated position and acceleration measurements of the first one of the two other sensors, and a second comparison between the computed acceleration of the second estimated position and acceleration measurements of the second one of the two other sensors; and digitally determining, with the computing device, which sensor has been arranged on the second body member and which sensor has been arranged on the third body member based on each of the first and second comparisons.

The person might inadvertently swap the sensors when placing them thereon, thus even though the sensors are on the expected body members, the computing device carrying out the motion tracking procedure provides an incorrect movement determination because the arrangement of the sensors does not fulfill the arrangement stored thereon. With this method, the computing device may derive which sensor has been placed on which body member.

The computing device has stored thereon data indicative of the movement to be performed by the person, thus it can derive what is the motion to be expected from each one of the body members involved in the movement. Preferably, a position of either the end of the third body member not connected to the second joint or the end of the one of the first and second body members not connected to the first joint is known, and is preferably still or substantially still while the person performs the movement. The computing device processes the sensor measurements and computes the rotation undergone by each sensor providing the measurements. The rotations may be computed in several ways, for instance they may be computed as angle variations in a given time window, and in addition the angle variations may be computed considering the degree of freedom about which the body member is supposed to rotate. The computed rotations are then used to identify which sensor has been placed on the first body member, since that body member is the one that shall be subject to a greatest rotation (i.e. the angular variation is the greatest) among the rotations of the tracked body members due to the predetermined movement to be performed.

The remaining two other sensors are then identified in one of the two following manners.

In the first manner, the position of the first joint is estimated using the measurements of the already identified sensor (i.e. the sensor with greatest rotation). Then, the computing device computes the acceleration for that estimated position (with the second derivative) so that the same may be compared with the acceleration measurements of each of the remaining two sensors, which are yet to be identified relative to the body members tracked. With the respective first and second comparisons obtained, the computing device identifies both sensors because the comparisons are indicative of the placement of the sensors owing to the accelerations undergone by the respective sensors. As each of the two remaining body members is subject to a different acceleration, the computing device derives which one of the two sensors is on the second body member because the acceleration measurements on the second body member shall be similar to the computed acceleration, and then it derives that the remaining sensor is the sensor arranged on the third body member.

In the second manner, the first and second positions of the first and second two other sensors are estimated. The computing device uses the measurements of the already identified sensor for estimating each of the first and second positions, and also the measurements of the respective sensor of the two other sensors. The acceleration of each of the first and second estimated positions are then computed, and each of these two accelerations is compared with the acceleration measurements of the respective sensor of the two other sensors. As each of the two remaining body members is subject to a different acceleration, the computing device derives which one of the two sensors is on the second body member and which one is on the third body member using the results of these comparisons.

In some embodiments, both the first and second comparisons are digitally computed so that a result thereof is indicative of a level of similarity or dissimilarity between the respective computed acceleration of the estimated position and the acceleration measurements of the respective sensor of the plurality of sensors.

In some embodiments, the method further comprises digitally determining, with the computing device, the movement performed by the person based on one of the first and second comparisons corresponding to the computed acceleration of the estimated position of the sensor arranged on one of the second or third body members. In some of these embodiments, the computing device determines that a first predetermined movement has been performed by the person if the one of the first and second comparisons is above a predetermined threshold. In some of these embodiments, the computing device further determines that either the first predetermined movement has not been performed by the person or a second predetermined movement has been performed by the person if the one of the first and second comparisons is below the predetermined threshold.

In some embodiments: the position of the first joint is digitally estimated by processing measurements of the determined sensor (i.e. the sensor with the greatest computed rotation) and a first predetermined length; the first position is digitally estimated by processing measurements of both the determined sensor and the first one of the two other sensors and both the first and a second predetermined lengths; and the second position is digitally estimated by processing measurements of both the determined sensor and the second one of the two other sensors and both the first and second predetermined lengths. In some of these embodiments, the first and second positions are digitally estimated by further processing a factor in the form of a decimal number greater than 0 and smaller than 1. As previously mentioned, the first and second predetermined length values correspond to the first and second body members, particularly to lengths thereof, estimated or measured.

In some embodiments, the movement involves each of the first, second and third body members. In some embodiments, all the body members having a sensor arranged thereon form a kinematic chain.

The person can be requested to perform a movement through presenting means, e.g. a screen visually showing instructions or a representation of the movement, audio output means providing audio instructions or guidance of the movement, etc.

In some embodiments, the first body member is a body member different from an extremity.

A fourth aspect of the invention relates to a system for tracking movement of a person, comprising:

a plurality of sensors at least comprising first, second and third sensors each at least comprising an accelerometer and a gyroscope, a first one of the first, second and third sensors being arrangeable on a first body member of the person, a second one of the first, second and third sensors being arrangeable on a second body member of the person, and a third one of the first, second and third sensors being arrangeable on a third body member of the person, the first and second body members being connected by a first joint, and the third body member being preferably connected to one of the first and second body members by a second joint; and a computing device comprising at least one processor, at least one memory and means for transmitting and receiving data, the computing device being programmed to:

compute, for each sensor of the plurality of sensors, a rotation undergone by the sensor when the person has the plurality of sensors arranged thereon tracking the movement of the person and performs a movement involving the first body member and at least one of the second and third body members, the first body member undergoing a rotation greater than rotation/s of the second and/or third body members during the movement;

determine that the sensor with the greatest computed rotation is arranged on the first body member;

estimate, while movement of the person is tracked:

a position of the first joint, the position being estimated using measurements of the determined sensor; or a position of each of the two other sensors thereby providing first and second estimated positions, the first position being estimated using measurements of both the determined sensor and the first one of the two other sensors, and the second position being estimated using measurements of both the determined sensor and the second one of the two other sensors;

compute an acceleration of each estimated position while movement of the person is tracked;

compute:

if the estimated position is the position of the first joint, a first comparison between the computed acceleration of the estimated position and acceleration measurements of the first one of the two other sensors, and a second comparison between the computed acceleration of the estimated position and acceleration measurements of the second one of the two other sensors; or if the estimated position is the first and second estimated positions, a first comparison between the computed acceleration of the first estimated position and acceleration measurements of the first one of the two other sensors, and a second comparison between the computed acceleration of the second estimated position and acceleration measurements of the second one of the two other sensors; and determine which sensor has been arranged on the second body member and which sensor has been arranged on the third body member based on each of the first and second comparisons.

The system is configured to track movement of the person while the same performs a predetermined movement and determine the arrangement of the sensors on the different body members of the person by processing the measurements provided by the sensors.

In some embodiments, the computing device computes both the first and second comparisons so that a result thereof is indicative of a level of similarity or dissimilarity between the respective computed acceleration of the estimated position and the acceleration measurements of the respective sensor of the plurality of sensors.

In some embodiments, the computing device is further programmed to determine the movement performed by the person based on one of the first and second comparisons corresponding to the computed acceleration of the estimated position of the sensor arranged on one of the second or third body members. In some of these embodiments, the computing device determines that a first predetermined movement has been performed by the person if the one of the first and second comparisons is above a predetermined threshold. In some of these embodiments, the computing device further determines that either the first predetermined movement has not been performed by the person or a second predetermined movement has been performed by the person if the one of the first and second comparisons is below the predetermined threshold.

In some embodiments, the computing device estimates: the position of the first joint by processing measurements of the determined sensor and a first predetermined length; the first position by processing measurements of both the determined sensor and the first one of the two other sensors and both the first and a second predetermined lengths; and the second position by processing measurements of both the determined sensor and the second one of the two other sensors and both the first and second predetermined lengths. In some of these embodiments, the computing device estimates the first and second positions by further processing a factor in the form of a decimal number greater than 0 and smaller than 1.

In some embodiments, the system further comprises means for presenting a movement to be performed by the person. In some of these embodiments, the means comprise a screen and/or audio output means.

In some embodiments, the system further comprises user input means, and the computing device is further programmed to receive input for one or more of: the first predetermined length, the second predetermined length, and the factor. In some of these embodiments, the user input means comprise a touchscreen and/or a keyboard.

Similar advantages as those described for the third aspect of the invention also apply to this aspect of the invention.

A fifth aspect of the invention relates to a method for tracking movement of a person, the method comprising the steps of:

arranging a plurality of sensors of a motion tracking system on a body of the person, the plurality of sensors at least comprising first and second sensors each at least comprising an accelerometer and a gyroscope, the first sensor being arranged on a first body member of the person, and the second sensor being arranged on a second body member of the person, the first and second body members being connected by a first joint;

tracking movement of the person with the plurality of sensors;

digitally estimating, with a computing device, a position of either the first joint or the second sensor, the position of the first joint being estimated using measurements of the first sensor and the position of the second sensor being estimated using measurements of both the first and second sensors, and the position being estimated while movement of the person is tracked;

digitally computing, with the computing device, an acceleration of the estimated position while movement of the person is tracked;

digitally computing, with the computing device, a comparison between the computed acceleration of the estimated position and acceleration measurements of the second sensor; and digitally determining, with the computing device, the movement performed by the person based on the comparison.

In some embodiments, the step of digitally determining the movement comprises determining that a first predetermined movement has been performed by the person if the comparison is above a predetermined threshold. In some of these embodiments, the step of digitally determining the movement further comprises determining that either the first predetermined movement has not been performed by the person or a second predetermined movement has been performed by the person if the comparison is below the predetermined threshold.

In some embodiments, the comparison is digitally computed so that a result thereof is indicative of a level of similarity or dissimilarity between the computed acceleration of the estimated position and the acceleration measurements of the second sensor.

In some embodiments: the position of the first joint is digitally estimated by processing measurements of the first sensor and a first predetermined length; and the position of the second sensor is digitally estimated by processing measurements of both the first sensor and the second sensor and both the first and a second predetermined lengths. In some of these embodiments, the position of the second sensor is digitally estimated by further processing a factor in the form of a decimal number greater than 0 and smaller than 1.

In some embodiments, movement of the person is tracked with the plurality of sensors at least while the person performs a movement. In some of these embodiments, the movement involves the first and second body members.

In some embodiments, the first body member undergoes a rotation greater than a rotation of the second member during the movement.

In some embodiments, the first and second body members are, respectively: upper leg and lower leg; lower leg and upper leg; upper arm and lower arm; chest and upper arm; lower back and upper back; upper chest and head; upper chest and upper arm; lower chest and upper chest; lower arm and hand; hand and fingers; lower leg and foot; foot and toes; lower arm and upper arm; upper leg and chest; upper arm and chest; or head and chest.

In some embodiments, the first body member is a body member different from an extremity.

A sixth aspect of the invention relates to a system for tracking movement of a person, comprising:

a plurality of sensors at least comprising first and second sensors each at least comprising an accelerometer and a gyroscope, the first and second sensors being arrangeable on first and second body members of the person, respectively; and a computing device comprising at least one processor, at least one memory and means for transmitting and receiving data, the computing device being programmed to:

estimate either a position of a first joint connecting the first and second body members or a position of the second sensor when the person has the plurality of sensors arranged thereon tracking the movement of the person, the position of the first joint being estimated using measurements of the first sensor and the position of the second sensor being estimated using measurements of both the first and second sensors;

compute an acceleration of the estimated position while movement of the person is tracked;

compute a comparison between the computed acceleration of the estimated position and acceleration measurements of the second sensor; and determine the movement performed by the person based on the comparison.

In some embodiments, the computing device determines that a first predetermined movement has been performed by the person if the comparison is above a predetermined threshold. In some of these embodiments, the computing device further determines that either the first predetermined movement has not been performed by the person or a second predetermined movement has been performed by the person if the comparison is below the predetermined threshold.

In some embodiments, the computing device computes the comparison so that a result thereof is indicative of a level of similarity or dissimilarity between the computed acceleration of the estimated position and the acceleration measurements of the second sensor.

In some embodiments, the computing device estimates: the position of the first joint by processing measurements of the first sensor and a first predetermined length; and the position of the second sensor by processing measurements of both the first sensor and the second sensor and both the first and a second predetermined lengths. In some of these embodiments, the computing device estimates the position of the second sensor by further processing a factor in the form of a decimal number greater than 0 and smaller than 1.

Similar advantages as those described for the first and second aspects of the invention may also be applicable to the fifth and sixth aspects of the invention.

BRIEF DESCRIPTION OF THE DRAWINGS

To complete the description and in order to provide for a better understanding of the invention, a set of drawings is provided. Said drawings form an integral part of the description and illustrate embodiments of the invention, which should not be interpreted as restricting the scope of the invention, but just as examples of how the invention can be carried out. The drawings comprise the following figures.

DESCRIPTION OF WAYS OF CARRYING OUT THE INVENTION

Figure 1:
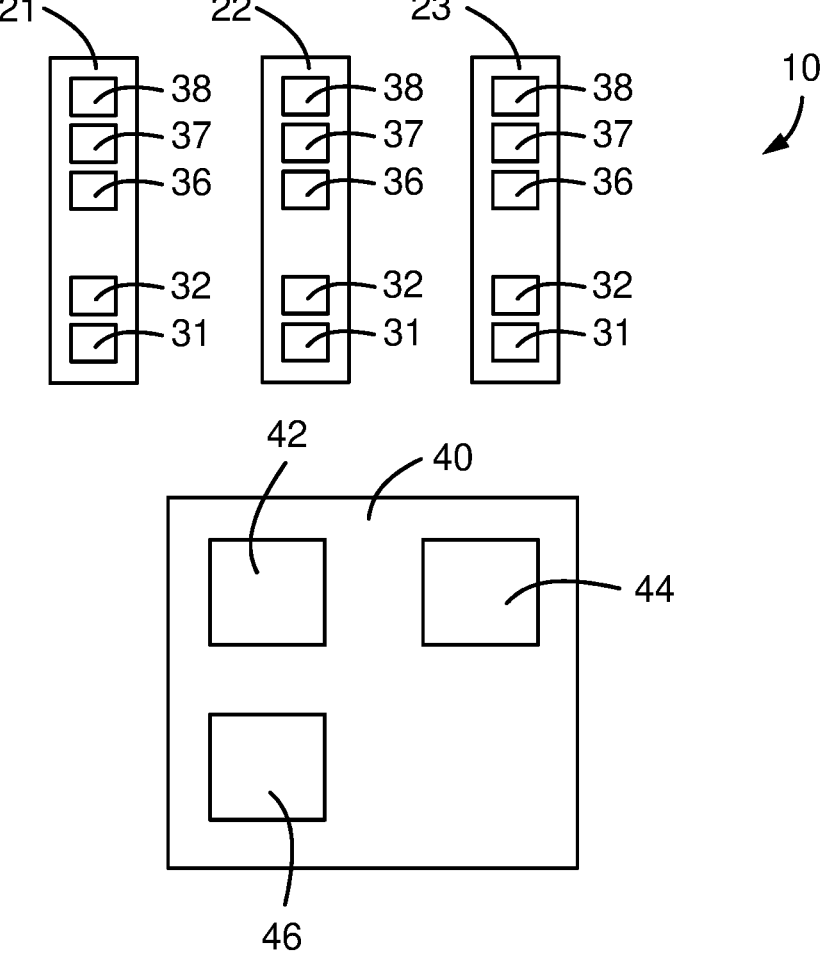
FIG. 1 diagrammatically shows a motion tracking system in accordance with an embodiment.

FIG. 1 diagrammatically shows a motion tracking system 10 in accordance with an embodiment. The motion tracking system 10 includes a plurality of sensors 21-23 and a computing device 40.

The sensors 21-23 are sensors that at least include a gyroscope 31 and an accelerometer 32. The sensors 21-23 also include at least one processor 36 and at least one memory 37. In preferred embodiments such as the one of FIG. 1, the sensors 21-23 further include a first communications module 38 for transmitting and receiving data that enables the sensors 21-23 to transmit (through a wired or wireless communications technology and protocol known by a skilled person, for instance but without limitation, Bluetooth communications, cellular network communications such as GSM, UMTS or LTE, wireless LAN communications, etc.) measurements of each of the sensing devices 31, 32 to the computing device 40. The same first communications modules 38 enable the sensors 21-23 to receive data from the computing device 40. In less preferred embodiments, the sensors 21-23 are not provided with the first communications module 38; in these embodiments, data can be extracted from the sensors 21-23 and/or provided to the sensors 21-23 by means of a computer readable storage medium.

The computing device 40 includes at least one processor 42 and at least one memory 44. Preferably, the computing device 40 further includes a second communications module 46 for transmitting and receiving data. When the computing device 40 is not provided with the second communications module 46, data can be extracted therefrom and/or introduced therein by means of a computer readable storage medium.

Figure 2:
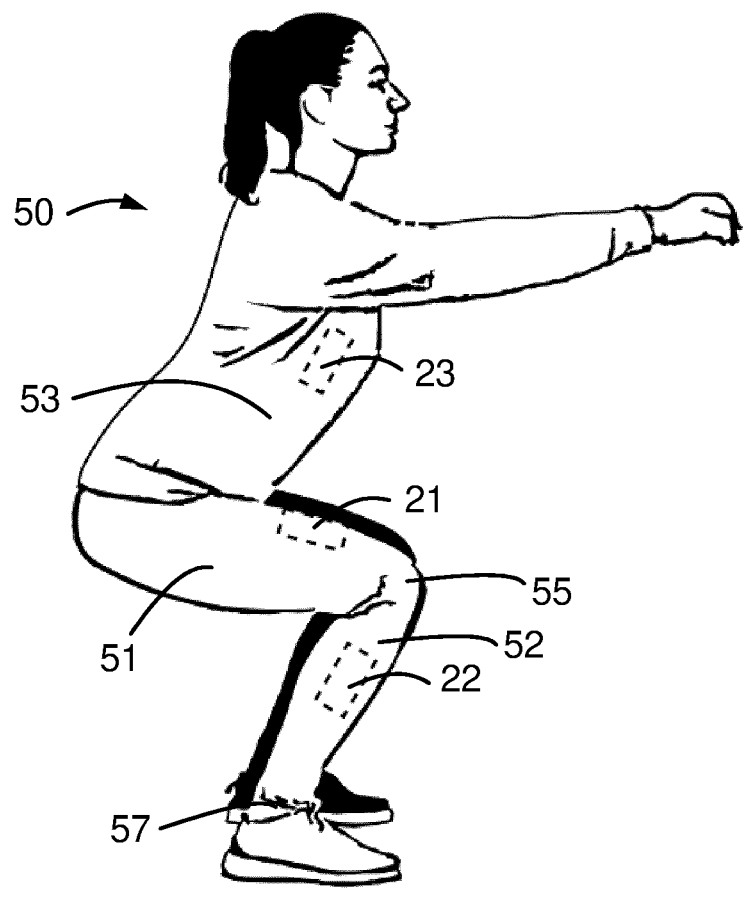
FIGS. 2-3 show a person performing predetermined movements while wearing motion tracking sensors.

FIG. 2 shows a person 50 performing a first predetermined movement while wearing sensors 21-23 of the motion tracking system 10.

The person 50 has arranged thereon three sensors 21-23 tracking the movement of said person: the first sensor 21 is on the right upper leg 51, the second sensor 22 is on the right lower leg 52, and the third sensor 23 is on the chest 53. These body members 51-53 form a kinematic chain.

In this example, the first predetermined movement is a squat, which involves the lower legs or shanks 52, and the upper legs or thighs 51, and the chest 53. In this movement, the end 57 of the lower legs 52 that connects to the ankle has a known position that remains still or almost still during the entire movement.

Figure 3:
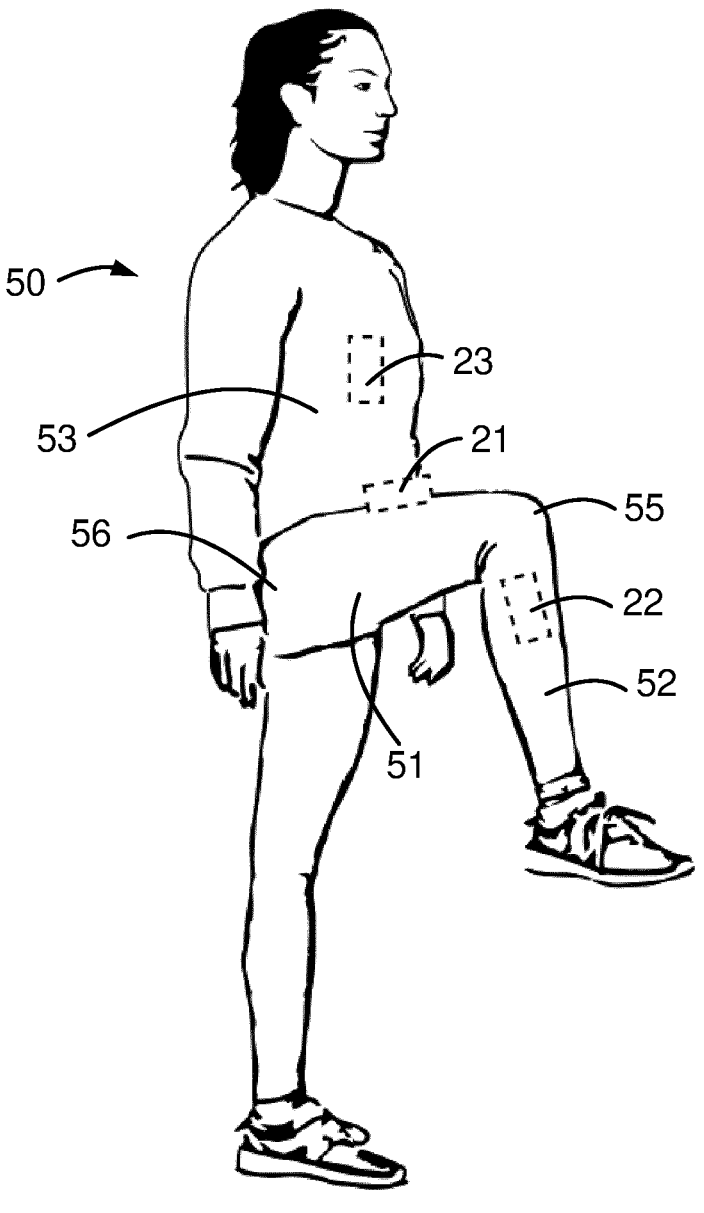

FIG. 3 shows the person 50 performing a second predetermined movement while wearing sensors 21-23 of the motion tracking system 10.

The person 50 has the three sensors 21-23 arranged as in FIG. 2, the difference of this example being that the second predetermined movement is a knee-up, which involves lower leg 52 and the upper leg 51 of a same leg. In this movement, the end 56 of the upper leg 51 that connects to the hip has a known position that remains still or almost still during the entire movement.

As it can be seen from FIGS. 2 and 3, at the most flexed position in the two physical exercises the chest 53, and the right upper and lower legs 51, 52 of a same leg have a similar angular arrangement despite the differences between the two movements.

If, as in the prior art, the orientations of the sensors 21-23 are used for determining the movement performed by the person, the angular relationship existing between the sensors 21-23 when the person 50 performs a first one of the two movements would be similar to that when the person 50 performs a second one of the two movements. In that case, it would not be possible to know whether, for example, the foot has been actually raised such that it leaves the ground or not, or if the hip has not moved. Just with the orientations measured while performing movements it is not possible to determine which one of the two movements has been performed. Methods and systems according to the present disclosure, however, make possible to determine the movement actually performed with a reduced probability of error.

Figure 4:
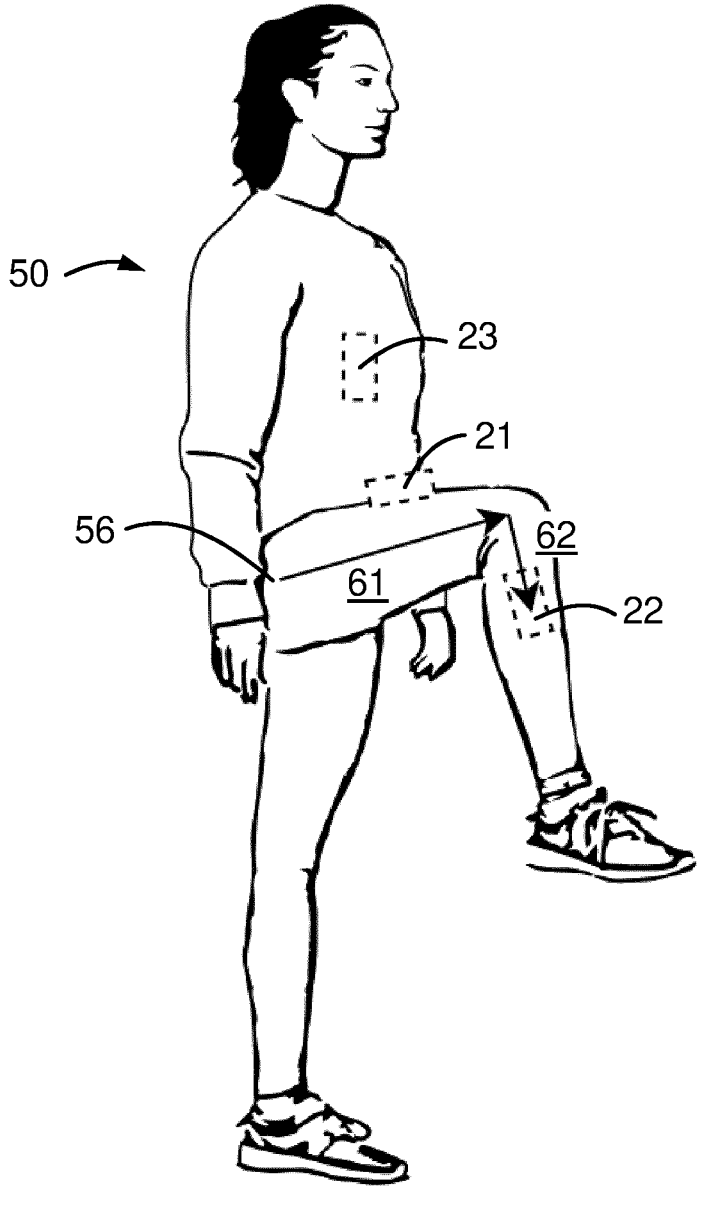
FIGS. 4 and 5 illustrate the estimation of the position in procedures in accordance with the present disclosure.

FIG. 4 illustrates the estimation of the position of a sensor 22 of the person 50 having arranged the sensors of the motion tracking system 10 thereon in accordance with a predetermined sensor arrangement, namely the sensors have not been swapped by mistake.

In this example, the person 50 is performing the movement of FIG. 3, namely a knee-up exercise.

The computing device 40 of FIG. 1 receives acceleration and orientation measurements from each sensor 21-23. By means of first and second orientations of the respective first and second sensors 21, 22, the position of the second sensor 22 on the right lower leg 52 is estimated.

Owing to the attachment of the first sensor 21 to the right upper leg 51, the first orientation 21 is indicative of the orientation of the right upper leg 51. With the first orientation 21, the position of the knee 55 is estimated with reference to the hip 56. This is achieved by processing the first orientation together with a value corresponding to a possible length of the right upper leg 51; this may be represented as the first vector 61 which is the result of combining said orientation and said length value. For the sake of clarity only, it can be considered that the orientation results in a unit vector (or an analogous mathematical tool) and the length value is the magnitude thereof.

Even though in this example the position of the hip 56 is known, the position of the knee 55 can also be estimated without knowledge of the position of the hip 56, in which case the position of the knee 55 is a position relative to the other endpoint of the first vector 61 (preferably made to coincide with the position of the hip 56 when this is known). Thus, as mentioned, the position of the knee 55 (which is a second endpoint of the first vector 61) is determinable by the computing device 40 relative to a first endpoint of the first vector 61.

From this estimated knee position, it is then estimated the position of the second sensor 22. This is achieved by processing the second orientation together with a value corresponding to a possible length of the right lower leg 52 times a factor (decimal value between 0 and 1 not including the endpoints) indicating the estimated position of the sensor 22 along the extension of the right lower leg 52. For instance, if the second sensor 22 is to be placed at the middle point of the right lower leg 52, the factor is 0,50, whereas if it is closer to the knee than to the ankle, the factor is less than 0,50 (but greater than 0,00). This combination may be represented as the second vector 62, which has its starting point at the estimated position of the knee. The estimated position of the second sensor 22 is then the combination of both vectors 61, 62, thus the position is referenced to the end of the right upper leg 51 with known position, hence referred to the hip 56.

As it is readily apparent, the first and second vectors 61, 62 have a direction based on the orientations provided by the respective sensors 21, 22. As the movement is performed, the orientations change and so does one or both of the estimated positions. Albeit in this example the computation for determining the movement performed is based on the estimated position of the second sensor 22, in other examples an equivalent computation could be based on the estimated position of the knee 55 because the estimated position thereof may vary similarly to the estimated position of the second sensor 22 (but if there is a further movement performed by the right lower leg 52, then the evolution of these two estimated positions differ in a greater degree).

The computing device 40 double differentiates the estimated position so as to obtain an acceleration of the estimated position. As the movement is performed by the person 50, the computing device 40 computes said acceleration. Then, by computing a comparison between the computed acceleration and the acceleration measurements of the second sensor 22, the computing device 40 determines that the movement actually performed by the person 50 is the knee-up instead of the squat of FIG. 2. This is so because the computed acceleration will be similar to the acceleration measurements of the second sensor 22, and thus the result of the comparison will be above a predetermined threshold set for determining that the movement performed is the knee-up, whereas if the squat had been performed the result of the comparison would not be above the predetermined threshold set. What is more, in this latter example, the computing device 40 could determine that since the predetermined threshold has not been exceeded, the movement performed by the person 50 is a squat, not just that the movement performed by the person 50 is not a knee-up.

The predetermined threshold is preferably set by carrying out tests for setting and/or adjusting the value of the predetermined threshold for given movements.

In this example, the computing device 40 has stored in the memory thereof that in a knee-up exercise the right lower leg 52 is to have an acceleration going upwards as the right upper leg 51 moves to a higher position, whereas in a squat exercise the right lower leg 52 has a reduced acceleration which, furthermore, does not go upwards but rather towards the front. Hence, if the person 50 is requested to perform a knee-up but instead the person 50 performs a squat, upon computing the comparison the computing device 40 will determine that no knee-up movement has been performed due to the differing accelerations. The same determination would be made by the computing device 40 if the estimated position to be double-differentiated were that of the knee 55 rather than the position of the second sensor 22.

In another example not illustrated, the computing device is configured to determine whether the movement performed by the person is a squat. In that example, the computing device preferably considers the lower leg as the first body member since one end thereof (i.e. the ankle) has a known position, which furthermore undergoes little or no movement at all while the squat is performed. The ankle position is thus preferably used as the referential for the processing of sensor measurements in order to determine if the movement performed is a squat.

Likewise, in yet another example in which it is attempted to determine whether the person performs a squat, the position of the knee is known or can be estimated thanks to, for example, measurements of the sensor on the lower leg. With the position of the knee as a reference, the computing device estimates the position of the hip or the position of the sensor on the chest. Then, the computing device computes an acceleration for said position and a first comparison between the computed acceleration and acceleration measurements of the sensor on the chest. Therefore, in this example, the upper leg and the chest are regarded as the first and second body members, respectively.

Figure 5:
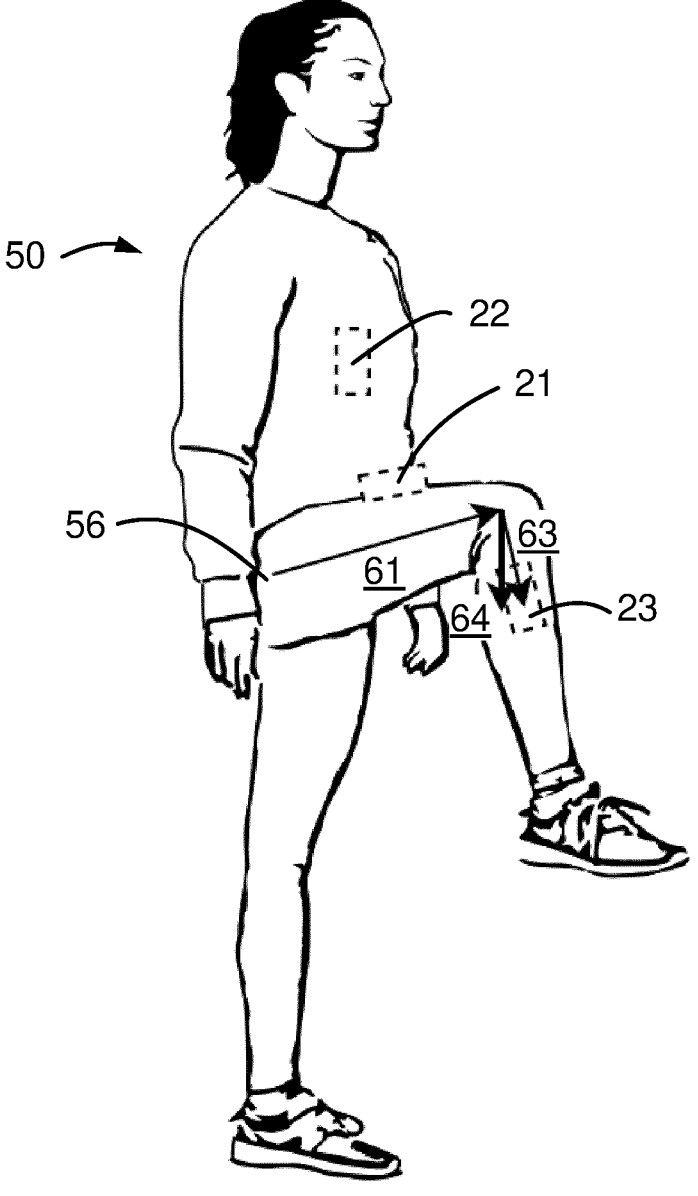

FIG. 5 illustrates the estimation of the position of a sensor 23 of the person 50 in order to determine if two sensors 22, 23 have been placed on the person swapped.

The person 50 is performing the knee-up movement once again. However, in this example the person 50 has inadvertently swapped the second and third sensors 22, 23; accordingly, the second sensor 22 is placed on the chest 53 whereas the third sensor is placed on the right lower leg 52.

If the computing device 40 is expecting a different sensor arrangement, e.g. the second sensor 22 on the right lower leg 52 and the third sensor 23 on the chest 53, because a different sensor and body member correspondence is stored in the memory of the computing device 40, the interchange of sensors 22, 23 will affect the determination of the movement performed by the person 50.

In this example, the computing device 40 attempts to estimate the position of the sensor arranged on the lower leg 52 using both sensors 22, 23 as potential candidates. The computing device 40 thus estimates a first position for that sensor by using measurements of both the sensor 21 that is arranged on the right upper leg 51 and a first one of the two sensors remaining, e.g. the second sensor 22, and also estimates a second position for the sensor arranged on the lower leg 52 by using measurements of both the sensor 21 that is arranged on the right upper leg 51 and a second one of the two sensors remaining, e.g. the third sensor 23. For clarity purposes only, the first estimated position at the particular time instant represented in FIG. 5 is at the end of the vector 64 (the direction of the vector 64 corresponding to the measurements provided by the second sensor 22, the length of the vector 64 corresponding to a second predetermined length intended to represent the distance at which the second sensor 22 is expected to be from the knee 55 should it have been arranged on the right lower leg 52, and the origin of the vector 64 at the estimated position 61 of the knee 55 is because the knee 55 is the joint connecting the right upper and lower legs 51, 52 that are involved in the movement), and the second estimated position at the particular time instant represented in FIG. 5 is at the end of the vector 63.

The accelerations of each of the first and second estimated positions are computed (taking the second derivative), and then each is compared to the acceleration measurements of the respective sensor of the two sensors 22, 23, thereby producing first and second comparisons. The computing device identifies which one of the two remaining sensors 22, 23 is placed on the right lower leg 52 by finding the comparison that has a greater degree of similarity between the computed acceleration and the acceleration measurements of one of the sensors (in this example, the third sensor 23), or conversely the comparison that has a lower degree of dissimilarity between the computed acceleration and the acceleration measurements of one of the sensors (i.e. the third sensor 23).

In some embodiments, after identifying which sensor is placed on the (second) body member connected to the (first) body member for estimating the position of the joint connecting both body members, the computing device 40 substitutes the measurements of, for example, the second sensor 22 for those of the third sensor 23 and/or vice versa, so that despite the incorrect placement of the sensors on the body of the person 50, the motion tracking procedure is continued without rendering incorrect the determination of the movement performed by the person 50. This process can be carried out before the process described with reference to FIG. 4.

With identified positions of the sensors 21-23, for example by way of the above procedure, the computing device of the motion tracking system is also capable of determining the movement performed by the person 50. In this case, the processing described with reference to FIG. 4 results in the determination of the movement, in this case a knee-up.

Figure 6:
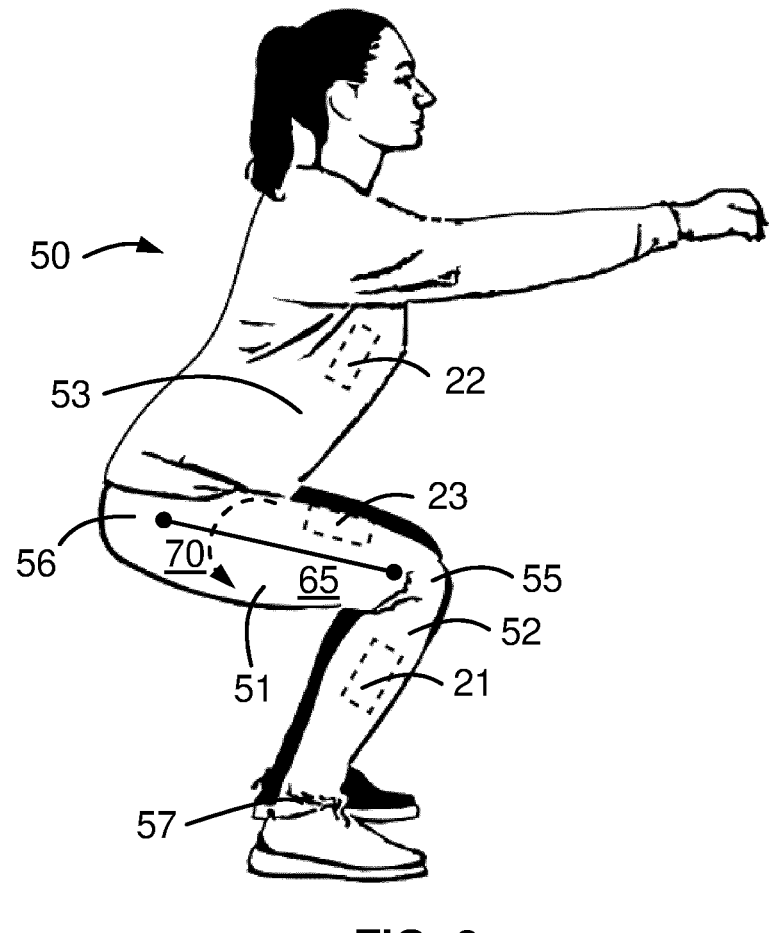
FIG. 6 illustrates a method for identifying sensors arranged on a person in accordance with an embodiment.

FIG. 6 illustrates a method for identifying the sensors 21-23 arranged on the person 50 in accordance with an embodiment.

The person 50 is performing the predetermined movement of a squat. Even though the person 50 intended to arrange the first, second and third sensors 21-23 on the right upper leg 51, right lower leg 52, and chest 53, respectively, the person 50 inadvertently swapped the sensors 21-23 and arranged the first sensor 21 on the right lower leg 52, the second sensor 22 on the chest 53, and the third sensor 23 on the right upper leg 51. The computing device of the corresponding motion tracking system 10 has stored thereon the intended sensor arrangement, thus the motion tracking procedure will not be correct.

The computing device 40 has stored thereon data indicative of how the body members would have to move during a squat movement. Accordingly, the data indicates that the right upper leg 51 is to be subject to a rotation 70 greater than rotations of both the right lower leg 52 and the chest 53, in this case the orientation 65 of the right upper leg 51 is about the knee 55 as shown with the dashed arrow 70.

The first, second and third sensors 21-23 provide measurements to the computing device 40, which in turn processes them to compute the rotations undergone by each one of the sensors 21-23 while the person 50 is performing the squat movement. The computing device 40 determines that the third sensor 23 is the sensor actually placed on the right upper leg 51 instead of the first sensor 21.

The computing device 40 estimates either the position of the knee 55 by testing the two possibilities because the position of the knee 55 is to be referenced to a known position, in this case the position of the ankle 57; the first possibility is the estimation using the measurements of the first sensor 21 and the second possibility is the estimation using the measurements of the second sensor 22. Alternatively, the computing device 40 computes first and second estimated positions corresponding to the expected position of the sensor on the right lower leg 52 by using the measurements of each of the two sensors different from the sensor identified as the sensor arranged on the right upper leg 51 (which in this example are the first and second sensors 21, 22) for the respective first and second positions. For estimating each of these positions, a predetermined length value corresponding to an estimated or measured length of the right lower leg 52 is used, and in the case of the first and second positions also a scale factor is used corresponding to the expected position of the sensor along the extension of the right lower leg 52. Then, the acceleration of the estimated position or the accelerations of the first and second estimated positions are computed.

The acceleration(s) computed is compared with the acceleration measurements of said two other sensors, thereby providing first and second comparisons. These comparisons are used for identifying the first and second sensors 21, 22. In this example, the computing device determines that the first sensor 21 is arranged on the right lower leg 52 because the acceleration measurements of that sensor are similar to the computed acceleration (of the estimated position for the knee 55), and determines that the second sensor 22 is the only sensor that may have been arranged on the chest 53.

Although the identification of the third sensor 23 as being the sensor arranged on the right upper leg 51 may not be attained until the movement is halfway performed or even completely performed by the person 50, all of the position(s) estimation, acceleration(s) computation and comparison(s) computation may be carried out with past measurements (the sensor measurements are stored on the memory of the computing device 40), therefore the computing device 40 is capable of completing the whole procedure when the movement is performed by the person 50, i.e. in the first squat each of the first, second and third sensors 21-23 are identified. In some embodiments, however, the computing device 40 may only identify the sensor on the right upper leg 51 when the movement is first performed, and identify the remaining sensors when the movement is repeated and, thus, additional sensor measurements are provided, i.e. in the first squat the third sensor 23 is identified, and in the second or further squats the first and second sensors 21, 22 are identified.

Also, in some embodiments, for the estimation of positions and subsequent computation of acceleration(s) as described with reference to FIGS. 4-6, a number of different measurements provided by the sensors are used for estimating the different positions so that the acceleration may be computed, for example five, ten, twenty, or even measurements of each sensor are used. Further, in some of these embodiments, said different measurements are taken when the movement performed by the person has reached or is about to reach an end position (such as the positions illustrated in FIGS. 2-6) so that the determination is made after or about completion of the movement; to this end, the computing device may compare the orientation measurements provided by one or more sensors with a predetermined movement limit threshold so as to derive whether the movement has reached or is about to reach such position. By way of example, if the knee-up movement is being performed, the predetermined movement limit threshold is e.g. 90 degrees, and the computing device compares the orientation of the right upper leg as measured by the sensor arranged thereon with said predetermined movement limit threshold to check if the leg has been raised as expected; when that occurs, the computing device takes the last e.g. five, ten, twenty, etc. measurements of the sensors to estimate the positions, compute the corresponding acceleration(s) and make the determination.

The comparison(s) described in relation to the process of FIGS. 4, 5 and 6 can be, for example but without limitation, any one of the following: the dot product between the two signals (i.e. the computed acceleration and the acceleration measurements of the corresponding sensor) in a given time window, the dot product in the frequency domain, the cross correlation between the two signals (evaluated at t=0), the mean squared difference, etc.

It is readily apparent that even if the examples described herein with reference to the FIGS. 2-6 refer to sensors 21-23 placed on the chest 53, right upper leg 51 and right lower leg 52, and the exercises are squats or knee-ups, other sensor placements and movements are possible within the scope of the present disclosure. In this respect, the computing device is to have stored in a memory thereof on which body members the plurality of sensors 21-23 is to be placed, and which movements are to be performed, together with a predetermined threshold and/or data indicative of the motion involved by the body members while the movement is performed, in this way the computing device is capable of determining the movement performed by the person 50 (i.e. by computing and comparing rotations, estimating position(s), computing the acceleration(s) associated therewith and comparing the computed acceleration(s) with the acceleration measurements in the manner described).

The following table shows a non-exhaustive list of placements of the first and second sensors 21, 22 and movements within the scope of the present disclosure; each row corresponds to a configuration for arranging the first and second body members 21, 22 and the possible movement(s) in such configuration:

| First body member with first sensor | Second body member with second sensor | Possible movements |
|---|---|---|
| Upper chest | Head | Any torso movement for which the hip position is constant (e.g. tilt, rotate, sit-ups) |
| Upper chest | Upper arm | Any torso movement for which the hip position is constant (e.g. tilt, rotate, sit-ups) |
| Lower chest | Upper chest | Any torso movement for which the hip position is constant (e.g. tilt, rotate, sit-ups) |
| Upper arm | Lower arm | Any upper arm movement for which the shoulder position is constant (e.g. flexion, abduction, rotation) |
| Lower arm | Hand | Any lower arm movement for which the elbow position is constant (e.g. flexing/extending the elbow, pronation/supination) |
| Hand | Fingers | Any hand movement for which the wrist position is constant (e.g. flexion/extension, ulnar/radial deviation) |
| Upper leg | Lower leg | Any upper leg movement for which the position of the hip is constant (e.g. hip flexion, hip abduction, donkey kicks) |
| Lower leg | Foot | Flex/extend the knee while the knee position is constant |
| Foot | Toes | Any foot movement for which the ankle position is constant (e.g. plantar flexion/dorsiflexion, inversion/eversion) |
| Lower leg | Upper leg | Any lower leg movement for which the position of the foot is constant (e.g. squat, lunges) |
| Lower arm | Upper arm | Any lower arm movement for which the position of the hand is constant (e.g. push-ups, sitting push-ups) |
| Upper leg | Chest | Any chest movement for which the position of the knee is constant (e.g. knee push-ups) |
| Upper arm | Chest | Any chest movement for which the position of the shoulder is constant (e.g. plank) |
| Head | Chest | Any chest movement for which the head is still (e.g. headstand) |

In each of the above possible placements of the first and second sensors 21, 22, the third sensor 23 may not be arranged on the person, or be arranged on any body member of the person, including a body member connected with the body member of the first sensor 21 or second sensor 22 by a joint different from that connecting the body members of the first and second sensor 21, 22.

The above configurations and movements are possible in respect of methods and systems according to any one of the first to the sixth aspects of the invention.

Even though the terms first, second, third, etc. have been used herein to describe several parameters, variables or devices, it will be understood that the parameters, variables or devices should not be limited by these terms since the terms are only used to distinguish one parameter, variable or device from another. For example, the first sensor could as well be named second sensor, and the second sensor could be named first sensor without departing from the scope of this disclosure.

In this text, the term "comprises" and its derivations (such as "comprising", etc.) should not be understood in an excluding sense, that is, these terms should not be interpreted as excluding the possibility that what is described and defined may include further elements, steps, etc.

On the other hand, the invention is obviously not limited to the specific embodiment(s) described herein, but also encompasses any variations that may be considered by any person skilled in the art (for example, as regards the choice of materials, dimensions, components, configuration, etc.), within the general scope of the invention as defined in the claims.

The invention claimed is:

1. A method for tracking movement of a person, the method comprising:
causing arrangement of a plurality of sensors of a motion tracking system on a body of the person, the plurality of sensors comprising a first sensor, a second sensor, and a third sensor, the first sensor, the second sensor, and the third sensor each comprising an accelerometer and a gyroscope, wherein the plurality of sensors are arranged in an unconfirmed arrangement on the body of the person;
tracking movement of the person with the plurality of sensors while the person performs a movement, the movement performed by the person involving a first body member of the person and at least one of a second body member of the person or a third body member of the person, the first body member and the second body member connected by a first joint, and the first body member undergoing a first rotation greater than a second rotation of at least one of the second body member or the third body member during the movement;
for each sensor of the plurality of sensors, digitally computing, with a computing device, a computed rotation undergone by the sensor while the movement of the person is tracked;
digitally determining, with the computing device, that the first sensor is arranged on the first body member based on the first sensor having a greatest computed rotation; and
digitally determining, with the computing device, that the second sensor is arranged on the second body member and the third sensor is arranged on the third body member by:

digitally estimating, with the computing device while the movement of the person is tracked, a first estimated position of the first joint, the first estimated position being estimated using first measurements of the first sensor and a first predetermined length;

digitally computing, with the computing device, a first computed acceleration of the first estimated position while the movement of the person is tracked; and digitally computing, with the computing device a first comparison between the first computed acceleration of the first estimated position and first acceleration measurements of the first sensor and a second comparison between the first computed acceleration of the first estimated position and second acceleration measurements of the second sensor; or digitally estimating, with the computing device while movement of the person is tracked, a second estimated position and a third estimated position, the second estimated position and the third estimated position estimated using the first measurements, second measurements of the second sensor, third measurements of the third sensor, a second predetermined length, and a third predetermined length;

digitally computing, with the computing device, a second computed acceleration of the second estimated position and a third computed acceleration of the third estimated position while the movement of the person is tracked; and digitally computing, with the computing device, a third comparison between the second computed acceleration of the second estimated position and second acceleration measurements of the second sensor and a fourth comparison between the third computed acceleration and third acceleration measurements of the third sensor.

2. The method of claim 1, wherein the second body member and the third body member are connected by a second joint.

3. The method of claim 1, further comprising digitally determining, with the computing device, the movement performed by the person based on the second comparison corresponding to the first computed acceleration of the first estimated position for the second sensor or the third comparison corresponding to the second computed acceleration of the second estimated position for the second sensor.

4. The method of claim 3, wherein the method further comprises determining that at least one of:

a first predetermined movement has been performed by the person if at least one of the first comparison, the second comparison, the third comparison, or the fourth comparison is above a predetermined threshold; or either the first predetermined movement has not been performed by the person or a second predetermined movement has been performed by the person if at least one of the first comparison, the second comparison, the third comparison, or the fourth comparison is below the predetermined threshold.

5. The method of claim 1, wherein the first body member, the second body member, and the third body member form a kinematic chain.

6. The method of claim 1, wherein both the first comparison and the second comparison are digitally computed to indicate a level of similarity or a level of dissimilarity between the first computed acceleration of the first estimated position and the first acceleration measurements of the first sensor or the second acceleration measurements of the second sensor.

7. The method of claim 1, wherein the first body member is a body member different from an extremity.

8. The method of claim 1, wherein digitally determining that the second sensor is arranged on the second body member and the third sensor is arranged on the third body member comprises:

digitally estimating, with the computing device while the movement of the person is tracked, the first estimated position of the first joint, the first estimated position being estimated using both first measurements of the first sensor and the first predetermined length;

digitally computing, with the computing device, the first computed acceleration of the first estimated position while the movement of the person is tracked; and digitally computing, with the computing device a fifth comparison between the first computed acceleration of the first estimated position and the second acceleration measurements of the second sensor and a sixth comparison between the first computed acceleration of the first estimated position and the third acceleration measurements of the third sensor.

9. The method of claim 1, wherein digitally determining that the second sensor is arranged on the second body member and the third sensor is arranged on the third body member comprises:

digitally estimating, with the computing device while movement of the person is tracked, the second estimated position and the third estimated position, the second estimated position and the third estimated position estimated using the first measurements, the second measurements of the second sensor, the third measurements of the third sensor, the second predetermined length, and the third predetermined length;

digitally computing, with the computing device, the second computed acceleration of the second estimated position and the third computed acceleration of the third estimated position while the movement of the person is tracked; and digitally computing, with the computing device, the third comparison between the second computed acceleration of the second estimated position and the second acceleration measurements of the second sensor and the fourth comparison between the third computed acceleration and the third acceleration measurements of the third sensor.

10. The method of claim 9, wherein the first estimated position and the second estimated position are digitally estimated by further processing a factor in a form of a decimal number greater than 0 and smaller than 1.

11. The method of claim 1, wherein each of the first comparison and the second comparison are computed using: a dot product between two compared signals in a given time window, a dot product between two compared signals in a frequency domain, a cross correlation between two compared signals evaluated at time equal zero, or a mean squared difference between two compared signals.

12. The method of claim 1, further comprising generating a request to the person to perform the movement.

13. A system for tracking movement of a person, comprising:

a plurality of sensors comprising a first sensor, a second sensor, and a third sensor, the first sensor, the second sensor, and the third sensor each comprising an accelerometer and a gyroscope; and a computing device comprising at least one processor and at least one memory, wherein the computing device is programmed to perform operations comprising:

causing arrangement of the plurality of sensors on a body of the person, wherein the plurality of sensors are arranged in an unconfirmed arrangement on the body of the person;

tracking movement of the person using the plurality of sensors while the person performs a movement, the movement performed by the person involving a first body member of the person and at least one of a second body member of the person or a third body member of the person, the first body member and the second body member connected by a first joint, and the first body member undergoing a first rotation greater than a second rotation of at least one of the second body member or the third body member during the movement;

for each sensor of the plurality of sensors, digitally computing a computed rotation undergone by the sensor while the movement of the person is tracked;

digitally determining that the first sensor is arranged on the first body member based on the first sensor having a greatest computed rotation; and digitally determining that the second sensor is arranged on the second body member and the third sensor is arranged on the third body member by:

digitally estimating, while movement of the person is tracked, a first estimated position of the first joint, the first estimated position being estimated using first measurements of the first sensor and a first predetermined length;

digitally computing a first a first computed acceleration of the first estimated position while the movement of the person is tracked; and digitally computing a first comparison between the first computed acceleration of the first estimated position and first acceleration measurements of the first sensor and a second comparison between the first computed acceleration of the first estimated position and second acceleration measurements of the second sensor; or digitally estimating, while movement of the person is tracked, a second estimated position and a third estimated position, the second estimated position and the third estimated position estimated using the first measurements, second measurements of the second sensor, third measurements of the third sensor, a second predetermined length, and a third predetermined length;

digitally computing a second computed acceleration of the second estimated position and a third computed acceleration of the third estimated position while the movement of the person is tracked; and digitally computing a third comparison between the second computed acceleration of the second estimated position and the second acceleration measurements of the second sensor and a fourth comparison between the third computed acceleration and third acceleration measurements of the third sensor.

14. The system of claim 13, wherein the second body member and the third body member are connected by a second joint.

15. The system of claim 13, the operations further comprising digitally determining, with the computing device, the movement performed by the person based on the second comparison corresponding to the first computed acceleration of the first estimated position for the second sensor or the third comparison corresponding to the second computed acceleration of the second estimated position for the second sensor.

16. The system of claim 15, the operations further comprising determining that at least one of:

a first predetermined movement has been performed by the person if at least one of the first comparison, the second comparison, the third comparison, or the fourth comparison is above a predetermined threshold; or either the first predetermined movement has not been performed by the person or a second predetermined movement has been performed by the person if at least one of the first comparison, the second comparison, the third comparison, or the fourth comparison is below the predetermined threshold.

17. The system of claim 13, wherein the first body member, the second body member, and the third body member form a kinematic chain.

18. The system of claim 13, wherein both the first comparison and the second comparison are digitally computed to indicate a level of similarity or a level of dissimilarity between the first computed acceleration of the first estimated position and the first acceleration measurements of the first sensor or the second acceleration measurements of the second sensor.

* * * * *